United States Patent [19]

Siuta-Mangano et al.

[11] Patent Number: 4,793,993

[45] Date of Patent: Dec. 27, 1988

[54] CROSSLINKING OF HAIR THIOLS

[75] Inventors: Patricia Siuta-Mangano, Valley Cottage, N.Y.; Herbert Edelstein, Stratford, Conn.

[73] Assignee: Chesebrough-Pond's Inc., Greenwich, Conn.

[21] Appl. No.: 88,356

[22] Filed: Aug. 24, 1987

Related U.S. Application Data

[63] Continuation-in-part of Ser. No. 69,929, Jul. 6, 1987.

[51] Int. Cl.$^4$ .............................. A61K 7/00; A61K 7/06
[52] U.S. Cl. .......................................... 424/70; 424/47; 424/71; 514/544; 514/569; 560/124; 560/132; 560/157; 560/164
[58] Field of Search .................. 424/70, 47, 71; 514/544, 569; 560/124, 132, 157, 169

[56] References Cited

U.S. PATENT DOCUMENTS

| | | | |
|---|---|---|---|
| 2,615,783 | 10/1952 | Haefele et al. | 8/128 |
| 2,739,033 | 3/1956 | Lubs | 8/128 |
| 2,850,351 | 9/1958 | Moore et al. | 8/127.6 |
| 2,933,365 | 4/1960 | Moore | 8/127.6 |
| 3,098,693 | 7/1983 | Sheehan | 8/127.6 |
| 3,537,809 | 11/1970 | Cedmas et al. | 8/127.6 |
| 3,766,302 | 6/1973 | Holub et al. | 260/884 |
| 3,833,609 | 9/1974 | Ladd | 260/326.26 |
| 3,912,806 | 10/1975 | Sokol | 424/71 |
| 4,049,007 | 9/1977 | Russell et al. | 132/7 |
| 4,134,895 | 1/1979 | Roth et al. | 260/326.41 |
| 4,175,572 | 11/1979 | Hsiung et al. | 132/7 |
| 4,218,539 | 8/1980 | Weltman | 435/188 |
| 4,251,445 | 2/1981 | Weltman | 260/326.4 |
| 4,390,525 | 6/1983 | Yosioka et al. | 424/71 |
| 4,424,820 | 1/1984 | Cannell et al. | 424/72 |

OTHER PUBLICATIONS

Cosmetics, Science and Technology, Edited by E. Sagarin, vol. 2, p. 230 (1972), Wiley Interscience.

The Science of Hair Care, Edited by Charles Zviak, vol. 7 of series entitled "Dermatology" (1986), Marcel Dekker, Inc., pp. 183–212.

Primary Examiner—George F. Lesmes
Assistant Examiner—P. J. Ryan
Attorney, Agent, or Firm—Melvin H. Kurtz

[57] ABSTRACT

Keratinous material, such as human hair, in which disulfide linkages have been ruptured to form disulfide linkages can be set using diimidates, and disuccinimidyl compounds as disclosed herein.

24 Claims, No Drawings

CROSSLINKING OF HAIR THIOLS

CROSS REFERENCE TO RELATED APPLICATION

This application is a continuation-in-part of application Ser. No. 069,929, filed Jul. 6, 1987.

The present invention relates to the treatment of keratinous materials to effect improvements in permanent waving or straightening.

BACKGROUND OF THE PRESENT INVENTION

Keratinous material, which occurs in animal hair, such as human hair consists of long polypeptide chains crosslinked to one another by means of occasional disulfide linkages. The disulfide linkages act to hold the hair in a permanent shape or configuration. Disruption of the disulfide linkages permits the polypeptide chains to function independently, allowing for the deformation of the shape of the hair without elasticity. Rupture of disulfide linkages may be accomplished by the use of various reducing agents, such as inorganic sulfides, sulfites, hydrosulfites and cyanides, mercaptans, thioglycolic acids, and various other compounds. Sulfhydryl groups are formed in place of the disulfide linkages.

In the cold-waving of hair, reduction of the disulfide linkages in hair is commonly performed in order to produce a permanent set, as in permanent waving, curling, or de-kinking of hair. The shaping of hair has conventionally been carried out by contacting the hair with a reducing agent in the form of liquids, creams, or gels while the hair has been mechanically formed into the desired new shape. The reducing composition is applied to the hair for a sufficient time to allow shaping to occur by the reductive disruption of the disulfide linkages. The reducing composition is then washed from the hair, and the normal resilience of the hair may then be regained by restoring the crosslinkages either by means of oxidizing agents or by treatment with the various crosslinking agents.

The restoration of the disulfide linkages is important in order to increase tensile strength, as well as remove the sulfhydryl groups as reactive sites. The desired crosslinking may be obtained by oxidation, as by heating in the presence of hair or by reacting with hydrogen peroxide solution. Bromates are frequently employed as oxidizing agents in the setting of permanently waved hair. Valuable properties may also be secured by the use of crosslinking agents, such as alkylene dihalides or dihalocarboxylic acids (U.S. Pat. No. 2,739,033) or dimaleimides (U.S. Pat. No. 2,850,351). By the use of crosslinking agents, it is possible to convert sulfhydryl linkages to cross linkages.

If permanent straightening of the hair is desired, the reducing lotion is generally applied in a thickened form such as, for instance, in a cream, and evenly distributed throughout the hair by combing. The hair is combed more or less continuously and maintained in a straightened condition for a period of time sufficient to allow rupture of the disulfide linkages. The shaping agent is then washed out with water and the set is then fixed as with an oxidizing agent or a crosslinking agent.

Many of the crosslinking agents which have been proposed heretofore are not water-soluble and must be used in the form of emulsions. Some of these agents are toxic and thus difficult to employ. Others are volatile and present a hazard to people using the same. Other crosslinking reagents not encumbered by the difficulties of past reagents is desirable.

BRIEF SUMMARY OF THE INVENTION

In accordance with the present invention, it has been found that keratinous materials in which disulfide linkages have been ruptured by the action of a reducing agent can be treated to establish cross linkages between keratin molecules by the application of an amount of a crosslinking reagent as specified herein sufficient to effect the desired treatment.

While a wide group of keratinous fiber can be treated in accordance with the present invention, including animal hair such as camel hair, mohair, wool, horsehair, cattle hair, hog bristles and the like; and feathers, such as from chicken, duck, turkey and the like, the invention is particularly directed to waving human hair whether in vivo or in vitro, i.e., in the form of wigs. The invention is particularly directed to "cold waving" and hair straightening systems and will be discussed in connection therewith.

DETAILED DESCRIPTION OF THE INVENTION

The reducing agents most commonly used in cold waving hair lotions for rupturing cystine linkages are thiols or mercaptans as well as sulfites and/or bisulfites. A number of mercaptans can only provide acceptable efficiency at high pH whereas others with a lower pH and a high ionization constant can be effective at lower pH levels. For example, the ammonium salt of thioglycolic acid can provide acceptable waving efficiency (reduction) if the pH of the solution exceeds 9. Other compounds such as thioglycolamides or glycol thioglycolates, sulfites and/or bisulfites can be used at neutral or even slightly acidic pH. The following are mercaptans and thiols which have commonly been used in cold waving lotions: thioglycolic acid, thiolactic acid, cysteine, thioglycerol, thioglycolic hydrazide, thioglycolamide, glycerol monothioglycolate, beta-mercaptopropionic acid, N-hydroxyethyl mercapto-acetamide, N-methyl mercapto-acetamide, beta-mercapto-ethylamine, beta-mercaptopropionamide, 2-mercapto-ethanesulfonic acid, dimercaptoadipic acid, dithiothreitol, homocysteinethiolactone, cysteine derivatives, and polythiol derivatives formed by the addition of cysteamine onto a maleic anhydridealkylvinylether copolymer. The sulfites and/or bisulfites which can be used are those normally used in hair waving such as the sodium and ammonium salts. The amount of the reducing agent used is that sufficient to rupture a sufficient number of disulfide bonds for effective hair waving or hair straightening as would be appreciated by one of ordinary skill in the art.

By the breaking of the disulfide bonds to form free sulfhydryl groups pendent on the hair, the hair can be formed or shaped as desired such as by winding on rollers or pins, or combed out as in the case of hair straightening. The breaking of the disulfide bonds is generally accomplished in accordance with the usual practice, which involved applying the reducing agent to the hair wound on curlers. Heat can be provided at this point.

The deformed hair, while curled or straightened, is then wetted with a crosslinking composition containing (1) diimidates of the formula:

$$R_1-O-C(NH)-R-C(NH)-O-R_1$$

and (2) disuccinimidyl compounds of the formula:

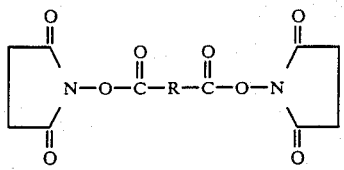

and mixtures thereof, wherein R represents a connecting moiety and $R_1$ represents an alkyl of 1 to 10 carbons.

The R radicals include, but are not limited to, any divalent connecting radicals which may be aliphatic, cycloaliphatic or aromatic or a combination of these moieties. Aliphatic includes alkylene ($-C_nH_{2n}-$) wherein n can be from 1 to 10 such as methylene; alkylidene ($C_{n-1}H_{2n-1}CH=$) where n can range from 1 to 10 such as ethylidene; aromatic includes phenylene, cyclohexylphenylene, tolylene, xylylene, naphthylene; aminophenylene; cycloaliphatic includes cyclohexylene, methylcyclohexylene, ethylcyclohexylene, and phenyl cyclohexylene. R can also include substituted radicals containing, for example, carboxyl groups, sulphonic groups, amino groups, amido groups, hydroxyl groups and the like, as well as ethers ($-R_x-O-R_x-$) and amines ($-R_x-NH-R_x-$). Numerous other divalent connecting radicals as would be obvious to one of ordinary skill are included within the representation of R. Relative to the diimidates, R is preferably alkylene; and relative to the disuccinimidyl compounds, R is preferably alkylene.

It is preferred that the crosslinking reagents of the invention be water soluble and, if necessary, contain a moiety to assist in making the compound water soluble such as an alkali metal sulfonyl group attached to R or the succinimidyl ring or quaternary ammonium group such as that normally used in hair waving systems (such as those disclosed In U.S. Pat. No. 3,912,808, the disclosure of which is incorporated herein by reference). Preferably, the water solubilization group is attached to any group which is split off in the crosslinking reaction so that the byproduct remains water soluble and can be washed out of the hair with water such as the N-succinimidyl radical. The water-solubilizing groupccan be in the form of a salt such as an alkali metal salt (Na.K) preferably sodium.

The crosslinking reagent can be used in water or in a carrier or base such as a lotion or cream, preferably buffered. The carriers are of known types and are similar to those presently in use in waving and "neutralizing" compositions. The water or carrier desirably holds the crosslinking reagent in contact with the hair for a period of time sufiicient to effect permanent setting of the hair. The crosslinking reagent is applied under conditions conducive to effecting crosslinking. A pH of between about 6 and about 9 (less than that which would cause permanent breakdown of the hair protein) has been found effective for that purpose using the compound of the invention.

The crosslinking reagent is preferably applied to the hair in a buffered system, and particularly a buffered system designed to maintain the pH between about 6 and about 9, and preferably between about 7 and about 8. Any or a combination of alkali metal phosphates, acetates, borates and the like which are non-reactive with the crosslinking reagent to thus destroy crosslinking sites, oan be used to maintain the pH of the hair treated with the crosslinking composition within the range specified. Any pH effects caused by the reducing agent can be offset by thorough washing of the hair with water prior to the application of the crosslinking composition.

The crosslinking composition can also contain a wetting agent or surfactant which is non-reactive with the crosslinking reagent or the hair to destroy crosslinking sites. The surfactant can be anionic, such as soaps, and alkyl sulfates, such as sodium dodecyl sulfate; cationic such as quaternary ammonuum compounds; nonionic, such as glycol esters, glycerol esters, sorbitan esters, polyoxyalkalene esters, polyoxyalkalene ethers, and modified lanolin, as well as amphoteric surfactants. One of the preferred surfactants is sodium dodecyl sulfate. The surfactant is used in an amount sufficient to assist in wetting the hair with the crosslinking reagent. The amount depending on the efficiency of the surfactant.

The crosslinking reagents can be applied to the hair alone after reduction or in combination with a reducing agent that is compatible with the crosslinking reagent. The use of the single-step system allows for the reduction and immediate crosslinking of the sulfhydryl groups.

The hair is treated for a period of time sufficient to effect the crosslinking to provide the curl and, in some instances, tensile strength increases desired. Illustrative times include from about 3 minutes to any practical, nondeterioration of the hair, upper limit though lesser times can be used if lesser effect on the hair is desired.

The crosslinking reagent is preferably applied in aqueous solution at a temperature between the ranges of about 10° C. (50° F.) and 93° C. (200° F.). Time of treatment may vary within wide limits depending on the temperature of the solution, the particular reducing and crosslinking agents used, and the nature of the keratinous material being treated.

The hair can be further treated with presently used neutralizing agents and crosslinking reagents in order to oxidize any free SH groups to disulfide linkages as would be appreciated by one of ordinary skill in the art. The oxidizing or neutralizing chemicals used can be any of the oxidizing agents capable of restoring the disulfide linkages in the hair keratin during the resetting stage, such as aqueous solution of hydrogen peroxide, alkali metal bromates, alkali metal perborates, urea, hydrogen peroxide, sodium sesquicarbonate, etc. Rinsing alone with water may restore the broken linkages as well, but it will be much slower.

The permanent waving system of the invention can be designed for professional and home application. The system and its compositions can contain ingredients normal to such compositions. Fragrance compounds, coloring agents, thickening agents, opacifying agents, sequestering agents, solubilizing agents, gelling agents, conditioning agents, etc., may be added to compositions of this invention in amounts conventionally used in hair waving and straightening compositions. Any compound which will react with the crosslinking reagent to remove or neutralize reactive sites thereon is preferably avoided. These ingredients are fully outlined in The Science of Hair Care, edited by Charles Zviak, Vol. 7 of a series entitled Dermatology, Marcel Dekker, Inc. 1986, which is incorporated herein by reference.

As used herein, the term "% weight per voIume" is intended to mean "grams per 100 milliliters".

The present invention is more fully illustrated in the Examples which follow.

All neutralization (reoxidation), unless otherwise stated, was performed using the neutralizer provided with the commercial waving lotion used in the examples for 5 minutes. All rinsing was performed with running water for 2 minutes. All times are in minutes.

EXAMPLE 1

Swatches (40 milligrams; 20.3 centimeters in length) of European brown Caucasian hair Wrapped around microrods were treated with a commercially available thioglycolate waving lotion (CLAIROL® Professional Kind to Hair Perm System) for 20 minutes to rupture the disulfide bonds. These swatches were then rinsed with running tap water. Some of the swatches were then placed into tubes containing 0.5 milliliter of a solution of 100 milligrams disuccinimidyl suberate (DSS) dissolved in 1 milliliter of dimethylformamide and 5 milliliters of a 50 millimolar sodium phosphate buffer (pH 8) containing 2% sodium dodecyl sulfate for 35 minutes; rinsed, neutralized and finally rinsed.

Hair swatches cut to 17.8 centimeters were analyzed for hanging curl length immediately after unrolling the hair swatches, after 2 hours of gentle drying, after 1 hour of soaking in 4 liters of tap water containing a few drops of 29% sodium dodecyl sulfate, and after another 2 hours of drying. The lengths in solution were measured while the hair remained in the solution. Curl lengths comparable to or better than that obtained using the commercial hair waving system as control were seen using disuccinimidyl suberate.

In the following results, which are the average of 2 experiments, a difference of 0.5 centimeters is considered significant.

TABLE I

| | Curl Length (centimeters) | | | |
| --- | --- | --- | --- | --- |
| | Wet 0 hr. | Dry 2 hr. | Solution 1 hr. | Dry 2 hr. |
| (Control) Commercial waving lotion with neutralization | 11.7 | 12.7 | 3.3 | 15.2 |
| DSS with neutralization | 10.4 | 11.4 | 1.27 | 12.7 |

EXAMPLE 2

Swatches (0.5 gram; 20.3 centimeters in length) of European brown Caucasian hair wrapped around commercially available curling rods were treated with a thioglycolate reducing system of the CLAIROL® Waving System for 20 minutes, followed by rinsing, neutralizing and rinsing. In the various tests discussed below the swatches were all treated with the CLAIROL® reducing system for 20 minutes followed by a rinse in running water. One set of swatches was treated in test tubes with 2 milliliters per tube of a solution of 800 milligrams disuccinimidyl suberate (DSS) predissolved in 8 milliliters of dimethylformamide (DMF) and 20 milliliters per tube of 50 millimolar sodium phosphate buffer (pH 8) containing 2% sodium dodecyl sulfate. These tresses were held for 30 minutes and then water rinsed. The tresses in some of these tubes were then neutralized and rinsed.

Another set of tubes was run as the previous set but without the DSS for the same time periods. The following results were obtained.

TABLE II

| | Curl Length (centimeters) | | | |
| --- | --- | --- | --- | --- |
| | Wet 0 hr. | Dry 2 hr. | Solution 1 hr. | Dry 2 hr. |
| (Control) Commercial waving lotion with neutralization | 13.4 | 14.2 | 7.9 | 15.2 |
| DSS without neutralization | 12.7 | 14.0 | 11.9 | 15.7 |
| DSS with neutralization | 12.2 | 13.4 | 4.1 | 15.0 |
| DMF/buffer/SDS without neutralization | 15.0 | 14.5 | 11.4 | 16.5 |
| DMF/buffer/SDS with neutralization | 13.2 | 14.5 | 6.4 | 15.5 |

The relative humidity during the test was 35% and the temperature was 20° C.

EXAMPLE 3

Swatches of hair as prepared in Example 2 were treated with 10 milliliters of 1% weight/volume solutions of bis(sulfosuccinimidyl)suberate (BS), dimethyl adipimidate (DMA) and dimethyl suberimidate (DMS) in 100 millimolar sodium phosphate buffer (pH 8) containing 2% sodium dodecyl sulfate to effect crosslinking. The swatches of hair were treated with a thioglycolate reducing agent (CLAIROL®) for 20 minutes followed by a rinsing period. Some swatches were then treated with 10 milliliters of a crosslinking solution and rinsed and compared to a sample neutralized using the commercial neutralizer and a sample treated with a solution of buffer for 20 minutes followed by a 20 minute rinse. The swatches treated with the crosslinking reagent were not treated with neutralizer. The following results were obtained.

TABLE III

| | Curl Length (centimeters) | | | |
| --- | --- | --- | --- | --- |
| | Wet 0 hr. | Dry 2 hr. | Solution 1 hr. | Dry 2 hr. |
| Crosslinking Reagent | | | | |
| BS | 13.4 | 14.2 | 14.0 | 15.7 |
| DMA | 13.2 | 13.7 | 10.9 | 16.0 |
| DMS | 13.4 | 14.0 | 10.4 | 15.5 |
| Commercial waving lotion with neutralization | 14.0 | 14.2 | 9.1 | 15.7 |
| Buffer without neutralization | 14.7 | 15.0 | 14.0 | 15.2 |

It is noted that that results of the buffer without crosslinking reagent appear to give the best curl of this series. These anomalous results may have been due to an experimental error.

EXAMPLE 4

In accordance with the procedure of Example 3, the following tests were run using a thioglycolate waving lotion as in Example 3. In all examples, 10 milliliters were applied per rod. After crosslinking, neutralization or buffer treatment, the swatches of hair were rinsed for 2 minutes in running water.

TABLE IV

| Crosslinking Reagent | Crosslinking Time | Neutralization Time |
| --- | --- | --- |
| A 1% w/v DMA (pH 8) | 10 | — |
| B 0.75% w/v Sulfo-EGS (pH 7) | 10 | — |
| C 1% w/v DMS (pH 8) | 10 | — |
| D 1% w/v DMP (pH 8) | 10 | — |
| E Control - Com. Wav. no Neut. | — | — |

TABLE IV-continued

| Crosslinking Reagent | Crosslinking Time | Neutralization Time |
|---|---|---|
| F Control - Com. Wav. with Neut. | — | 5 |
| G Buffer (pH 7) - no Neut. (no crosslinker) | 10 | — |
| H Buffer (pH 8) - no Neut. (no crosslinker) | 10 | — |

Crosslinking compositions were prepared in 50 millimolar sodium phosphate buffer without sodium dodecyl sulfate. Sulfo-EGS means ethylene glycol-bis(sulfosuccinimidyl succinate) and DMP means dimethyl pimelimidate. Curling tests were run at 36% relative humidity and 18° C. (65° F.) with the following results.

TABLE V

| | Curl Length (centimeters) | | | |
|---|---|---|---|---|
| | Wet 0 hr. | Dry 2 hr. | Solution 1 hr. | Dry 2 hr. |
| A DMA (−N) | 14.2 | 14.7 | 8.6 | 16.5 |
| B Sulfo-EGS (−N) | 14.5 | 14.5 | 10.7 | 15.7 |
| C DMS (−N) | 13.7 | 14.2 | 10.2 | 16.3 |
| D DMP (−N) | 14.0 | 14.2 | 10.2 | 15.7 |
| E Control (−N) | 16.8 | 17.3 | 16.5 | 17.5 |
| F Control (+N) | 13.4 | 14.5 | 5.0 | 15.7 |
| G Buffer - pH 7 (−N) | 15.2 | 15.2 | 12.7 | 17.0 |
| H Buffer - pH 8 (−N) | 16.3 | 16.0 | 14.5 | 17.0 |

(+N) means with neutralization.
(−N) means without neutralization.

EXAMPLE 5

The procedure of Example 4 was repeated. The following samples were prepared. All solutions prepared using 2% w/v crosslinking reagent in 200 milliliters sodium phosphate buffer at pH 8.5. The crosslinking reagents or buffers were applied to swatches for 12 minutes. Samples were rinsed after crosslinking and neutralization.

TABLE VI

| Sample | Crosslinking Reagent | Neutralization With | Without |
|---|---|---|---|
| A | DMP | — | + |
| B | DMP | + | — |
| C | Control | + | — |
| D | Buffer | — | + |
| E | Buffer | + | — |

The samples were evaluated for curling at 27% relative humidity and a temperature of 21° C. (70° F.). The following results were obtained.

TABLE VII

| | Curl Length (centimeters) | | | |
|---|---|---|---|---|
| | Wet 0 hr. | Dry 2 hr. | Solution 1 hr. | Dry 2 hr. |
| A DMP (−N) | 13.7 | 14.2 | 8.1 | 16.3 |
| B DMP (+N) | 13.7 | 14.5 | 2.5 | 14.7 |
| C Control Waving (+N) | 13.2 | 14.5 | 7.6 | 15.2 |
| D Buffer (−N) | 15.0 | 15.0 | 12.7 | 17.0 |
| E Buffer (+N) | 12.7 | 14.5 | 3.8 | 15.5 |

What is claimed is:

1. A process for treating keratinous material in which the disulfide linkages have been disrupted to form free sulfhydryl groups which comprises: contacting the keratinous material with a crosslinking reagent selected from the group consisting of (1) diimidates of the formula:

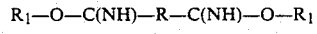

and (2) disuccinimidyl compounds of the formula:

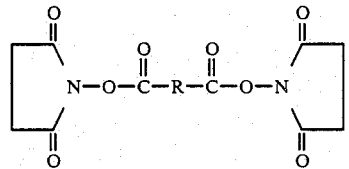

and mixtures thereof, wherein R represents a connecting moiety and $R_1$ represents an alkyl of 1 to 10 carbons, at a temperature and pH to form crosslinkages and insufficient to substantially denature the protein of the keratinous material.

2. The process as recited in claim 1 wherein the crosslinking is conducted at a pH between about 6 and about 9.

3. The process as recited in claim 1 wherein said keratinous material is human hair.

4. The process as recited in claim 3 wherein the hair is deformed to a desired shape prior to treatment with the crosslinking reagent.

5. The process as recited in claim 1 wherein said crosslinking reagent is water soluble.

6. A hair waving system comprising a composition for reducing disulfide bonds to form sulfhydral groups in hair and a crosslinking composition containing a crosslinking reagent selected from the group consisting of (1) diimidates of the formula:

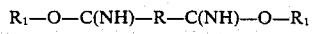

and
(2) disuccinimidyl compounds of the formula:

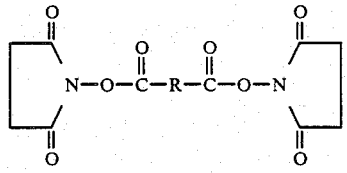

and mixtures thereof, wherein R represents a connecting moiety and $R_1$ represents an alkyl of 1 to 10 carbons.

7. The system as recited in claim 6 wherein said crosslinking reagent is water soluble.

8. A process for treating keratinous material in which the disulfide linkages have been disrupted by the action of a reducing agent forming free sulfhydryl groups comprising contacting the said keratinous material with a crosslinking reagent $R_1$—O—C(NH)—R—C(NH)—O—$R_1$ wherein R represents a connecting moiety and $R_1$ represents an alkyl of 1 to 10 carbon atoms, the process being conducted under conditions sufficient to form crosslinkages and insufficient to substantially denature the protein of the keratinous material.

9. A process for treating keratinous material in which the disulfide linkages have been disrupted by the action of a reducing agent forming free sulfhydryl groups comprising contacting the said keratinous material with a crosslinking reagent

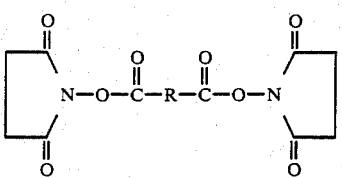

wherein R represents a connecting moiety, the process being conducted under conditions sufficient to form crosslinkages an insufficient to substantially denature the protein of the keratinous material.

10. The process as recited in claim 8 wherein R is alkylene of 1 to 10 carbons.

11. The process as recited in claim 10 wherein R is alkylene of 4 to 6 carbons.

12. The process as recited in claim 8 wherein $R_1$ is an alkyl of 1 to 2 carbons.

13. The process as recited in claim 9 wherein R is alkyl of from 1 to 10 carbons.

14. The process as recited in claim 8 wherein said crosslinking reagent is water soluble.

15. The process as recited in claim 9 wherein said crosslinking reagent is water soluble.

16. The process as recited in claim 9 wherein the crosslinking reagent is sulfonated for water solubility.

17. The process as recited in claim 1 wherein the crosslinking reagent is the hydrochloride salt for water solubility.

18. The process as recited in claim 1 wherein said diimidate compound is selected from the group consisting of dimethyl suberimidate, dimethyl adipimidate, dimethyl pimelimidate and mixtures thereof.

19. The system as recited in claim 6 wherein said diimidate compound is selected from the group consisting of dimethyl suberimidate, dimethyl adipimidate, dimethyl pimelimidate and mixtures thereof.

20. The process as recited in claim 1 wherein said disuccinimidyl compound is ethylene glycol bis(sulfosuccinimidyl succinate).

21. A process of claim 1 wherein R is a divalent connecting radical selected from the group consisting of aliphatic, cycloaliphatic aromatic or combination thereof and wherein R can be substituted with carboxyl, sulfonic, amino, amido, hydroxyl and can contain ether and amine linkages.

22. A system of claim 6 wherein R is a divalent connecting radical selected from the group consisting of aliphatic, cycloaliphatic aromatic or combination thereof and wherein R can be substituted with carboxyl, sulfonic, amino, amido, hydroxyl and can contain ether and amine linkages.

23. A process of claim 8 wherein R is a divalent connecting radical selected from the group consisting of aliphatic, cycloaliphatic aromatic or combination thereof and wherein R can be substituted with carboxyl, sulfonic, amino, amido, hydroxyl and can contain ether and amine linkages.

24. A process of claim 9 wherein R is a divalent connecting radical selected from the group consisting of aliphatic, cycloaliphatic aromatic or combination thereof and wherein R can be substituted with carboxyl, sulfonic, amino, amide, hydroxyl and can contain ether and amine linkages.

* * * * *